(12) United States Patent
Rodríguez De Fonseca et al.

(10) Patent No.: US 9,050,347 B2
(45) Date of Patent: Jun. 9, 2015

(54) 1,2,4-OXADIAZOLE DERIVATIVES AS DRUGS MODULATING THE GLP-1 PEPTIDE RECEPTOR

(75) Inventors: Fernando Antonio Rodríguez De Fonseca, Málaga (ES); Miguel Romero Cuevas, Málaga (ES); Laura Orio Ortíz, Málaga (ES); Juan Manuel Decara Del Olmo, Málaga (ES); Monica Alonso Scrignoli, Málaga (ES)

(73) Assignee: VIVIABIOTECH, S.L., Madrid (ES)

( * ) Notice: Subject to any disclaimer, the term of this patent is extended or adjusted under 35 U.S.C. 154(b) by 0 days.

(21) Appl. No.: 13/981,554

(22) PCT Filed: Jan. 25, 2011

(86) PCT No.: PCT/ES2011/070042
§ 371 (c)(1),
(2), (4) Date: Oct. 11, 2013

(87) PCT Pub. No.: WO2012/101292
PCT Pub. Date: Aug. 2, 2012

(65) Prior Publication Data
US 2014/0031347 A1    Jan. 30, 2014

(51) Int. Cl.
| A61K 31/541 | (2006.01) |
|---|---|
| A61K 31/454 | (2006.01) |
| A61K 31/4725 | (2006.01) |
| A61K 31/5377 | (2006.01) |
| A61K 31/4545 | (2006.01) |

(52) U.S. Cl.
CPC ............. *A61K 31/541* (2013.01); *A61K 31/454* (2013.01); *A61K 31/4725* (2013.01); *A61K 31/5377* (2013.01); *A61K 31/4545* (2013.01)

(58) Field of Classification Search
USPC ..................................... 514/227.8, 326, 318
IPC ...................................................... A61K 31/541
See application file for complete search history.

(56) References Cited

U.S. PATENT DOCUMENTS

| 7,799,782 B2 * | 9/2010 | Munson et al. ............ 514/234.5 |
| 7,838,682 B2 | 11/2010 | Nan et al. |
| 2006/0275288 A1 | 12/2006 | Grihalde et al. |

FOREIGN PATENT DOCUMENTS

| EP | 1695968 A1 | 8/2006 |
| WO | WO0135988 A1 | 5/2001 |
| WO | WO0189554 A2 | 11/2001 |
| WO | WO03011892 A2 | 2/2003 |
| WO | WO03084563 A1 | 10/2003 |
| WO | WO2005023291 A2 | 3/2005 |
| WO | WO2005056537 A1 | 6/2005 |
| WO | WO2006003096 A1 | 1/2006 |
| WO | WO2006123249 A2 | 11/2006 |
| WO | WO2007024700 A2 | 3/2007 |
| WO | WO2007120936 A2 | 10/2007 |
| WO | WO2007123581 A1 | 11/2007 |
| WO | WO2008030570 A1 | 3/2008 |
| WO | WO2008050200 A1 | 5/2008 |
| WO | WO2008081208 A1 | 7/2008 |
| WO | WO2008131149 A2 | 10/2008 |
| WO | WO2009085990 A2 | 7/2009 |
| WO | WO 2010080864 * | 7/2010 |

OTHER PUBLICATIONS

Goldfarb's CAS: 151:92846, 2009.*
Goldfarb's CAS: 151:92840, 2009.*
International Search Report and Written Opinion of the International Searching Authority. International Application No. PCT/ES2011/070042, issued by the Spanish Patent Office, mail date Jun. 20, 2011, Madrid Spain. (2 pages of the Spanish search report is included with an English translation by the PCT Authority together with the English translation of the written opinion also provided by the PCT Authority).
Astrup, Arne, "Effects of liraglutide in the treatment of obesity: a randomised, double-blind, placebo-controlled study", The Lancet, vol. 374, Issue 9701, pp. 1606-1616, Nov. 7, 2009, Elsevier Ltd, Waltham, MA.
Turner, Robert, et al, "United Kingdom Prospective Diabetes Study 17: A 9-Year Update of a Randomized, Controlled Trial on the Effect of Improved Metabolic Control on Complications in Non-Insulin-dependent Diabetes Mellitus, Annals of Internal Medicine", Annals of Internal Medicine, vol. 124, No. 1, Part 2, pp. 136-145, Jan. 1, 1996, American College of Physicians, Philadelphia, PA.
Turner, Robert et al., "Intensive blood-glucose control with sulphonylureas or insulin compared with conventional treatment and risk of complications in patients with type 2 diabetes (UKPDS 33)", The Lancet, vol. 352, Issue 9131, pp. 837-853, Sep. 12, 1998. Elsevier Ltd, Waltham, MA.

(Continued)

*Primary Examiner* — Rei-Tsang Shiao
(74) *Attorney, Agent, or Firm* — Peter B. Scull; Hamilton, DeSanctis & Cha LLC (57) ABSTRACT

The present invention relates to the use of a compound of formula (I):

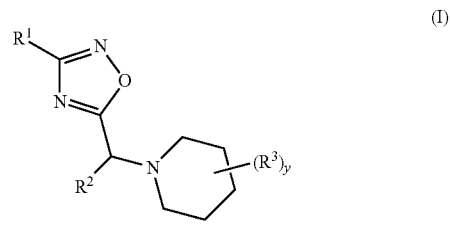

or a pharmaceutically acceptable solvate or salt thereof in the preparation of a medicinal product for the prevention and/or the treatment of a disease in which the GLP-1 receptor participates or mediates, such as eating disorders or diseases, for example, obesity, anorexia, lipid dysfunction, diabetes, hyperinsulinism and cardiovascular diseases or metabolic syndrome.

11 Claims, 4 Drawing Sheets

(56) References Cited

OTHER PUBLICATIONS

Nathan, D.M. et al., "Management of hyperglycaemia in type 2 diabetes: a consensus algorithm for the initiation and adjustment of therapy", Diabetologia, vol. 49, Issue 8, pp. 1711-1721, Aug. 2006, Springer-Verlag, Berlin Germany.

Turner, Robert et al., "Effect of intensive blood-glucose control with metformin on complications in overweight patients with type 2 diabetes (UKPDS 34)", The Lancet, vol. 352, Issue 9131, pp. 854-865, Sep. 12, 1998, Elsevier Ltd, Waltham, MA.

Ma, Jing MD et al., "Insulin secretion in healthy subjects and patients with Type 2 diabetes—role of the gastrointestinal tract", Best Practice & Research Clinical Endocrinology & Metabolism, vol. 23, Issue 4, pp. 413-424, Aug. 2009, Elsevier Ltd, Waltham, MA.

Drucker, DJ, "The biology of Incretin Hormones", Cell Metabolism, vol. 3, Issue 3, pp. 153-165, Mar. 1, 2006, Elsevier Ltd, Waltham, MA.

Drucker, Daniel J. et al., "The incretin system: glucagon-like peptide-1 receptor agonists and dipeptidyl peptidase-4 inhibitors in type 2 diabetes", The Lancet, New Drug Class, vol. 368, Issue 9548, pp. 1696-1705, Nov. 11, 2006, Elsevier Ltd, Waltham, MA.

Thornberry, Nance A. PhD, et al., "Mechanism of action of inhibitors of dipeptidyl-peptidase-4 (DPP-4):", Science Direct Best Practice & Research Clinical Endocrinology & Metabolism, vol. 23, Issue 4, pp. 479-486, Aug. 2009, Elsevier Ltd, Waltham, MA.

Buse, John B. et al., "Liraglutide once a day versus exenatide twice a day for type 2 diabetes: a 26-week randomised, parallel-group, multinational, open-label trial (LEAD-6)" The Lancet, vol. 374, Issue 9683, pp. 39-47, Jul. 4, 2009, Elsevier Ltd, Waltham, MA.

Madsbad, Sten, "Exenatide and liraglutide: different approaches to develop GLP-1 receptor agonists (incretin mimetics)—preclinical and clinical results", Science Direct, Best Practice & Research Clinical Endocrinology & Metabolism, vol. 23, Issue 4, Aug. 2009, pp. 463-477, Elsevier Ltd, Waltham, MA.

Aulton, Michael E., "Pharmaceutics: The Science of Dosage Form Design / Edition 2", Limited, Dec. 5, 2002, pp. 1-704, Churchill Livingstone Elsevier, Edinburgh Scotland.

Swarbrick, James, "Encyclopedia of Pharmaceutical Technology, Second Edition", May 28, 2002, pp. 1-676, Taylor & Francis, New York, New York.

Banker, Gilbert S. et al., "Modern Pharmaceutics, Fourth Edition,: Basic Principles and Systems / Edition 4", Informa Healthcare, May 28, 2002, pp. 1-864, Marcel Dekker, New York, New York.

Lachman, Leon, et al., "The Theory and Practice of Industrial Pharmacy, Edition Three", The Journal of Clinical Pharmacology and the Journal of New Drugs, Nov. 28, 1986, pp. 1-902, Lippincott Williams & Wilkens, Philadelphia, PA.

Madsbad, Sten, "Remington: The Science and Practice of Pharmacy. 21st Edition", Lippincott Williams & Wilkins, May 1, 2005, pp. xxii-2393, Philadelphia, PA.

* cited by examiner

1,2,4-OXADIAZOLE DERIVATIVES AS DRUGS MODULATING THE GLP-1 PEPTIDE RECEPTOR

FIELD OF THE ART

The present invention relates to the use of a series of oxadiazole derivatives and the pharmaceutically acceptable solvates or salts thereof, which show capacity to modulate the biological responses mediated by the glucagon-like peptide type 1 (GLP-1) receptor. The compounds of the invention can activate, enhance or antagonize the functions regulated by the mentioned receptors, which include food intake control, body weight regulation, insulin secretion and carbohydrate metabolism regulation. These properties make them useful for the treatment of obesity, diabetes, hyperinsulinism and their associated diseases.

STATE OF THE ART

The GLP-1 receptor is known to be involved in multiple diseases and disorders, such as for example, eating disorders, such as for example, appetite inhibition, obesity (Lancet 2009, 374, 1606-1616) or cardiovascular diseases (WO2001089554, WO2003084563).

Type 2 diabetes is a progressive disease which is characterized by the presence of elevated blood glucose levels caused either by an insufficiency of the endocrine pancreas in the production of insulin or by the decrease of the sensitivity of body tissues to this hormone. There are more than 200 million people with type 2 diabetes worldwide and this figure is expected to increase to 350 million in 2030 (Annals of Internal Medicine 1996; 124: 136-145.). One of the reasons for this increase is the current obesity epidemic, which is considered to be the main risk factor for type 2 diabetes. The sustained hyperglycemia which diabetes patients have leads to micro- and macrovascular complications which will lead to a reduction in the life expectancy of diabetic patients since they cause renal failure, cardiac failure, peripheral angiopathy and neuropathy the final expression of which will be the necrosis of the limbs. The persistence of this sustained hyperglycemia can easily be controlled by measuring the blood glycated hemoglobin (HbA1c) levels (Lancet 1998; 352: 837-853).

Current therapies for type 2 diabetes are aimed at normalizing glycemia, reducing the HbA1c to 6%), with the long-term aim of preventing fatal consequences derived from the vascular damage associated with diabetes. This is achieved by means of multiple therapies aimed at reducing blood glucose or at increasing insulin secretion by the endocrine pancreas. The therapeutic algorithms for diabetes always start with therapies which reduce the glucose levels, in order to incorporate, as the disease progresses, therapies capable of increasing insulin release or of sensitizing its action. The most recommended current treatments are (Diabetologia 2006; 49: 1711-1721):
  a) Decreasing the hepatic production of glucose with metformin
  b) Decreasing the absorption of glucose with acarbose
  c) Increasing insulin release by means of sulfonylureas or metiglinides
  d) Decreasing insulin resistance with thiazolidinediones.
  e) Directly treating the disease with exogenously administered insulin.

All diabetes treatment algorithms start with metformin since it is the only medicinal product cheap, safe and with probable reduction of 15-year mortality (Lancet 1998; 352: 854-865), especially in obese patients. The only medicinal product retaining a higher efficacy over time than metformin is rosiglitazone, a thiazolidinedione, but its use causes a considerable weight gain. The second line of treatment corresponds to insulin-releasing drugs such as sulfonylureas and the metiglinides. They are cheap and safe, but cause hypoglycemias which are very inconvenient for the patient, as well as a body weight gain (Lancet 1998; 352: 837-853).

The treatment algorithms become complicated since these drugs lose efficacy over time, so combined treatments with more than one drug from the previous groups are chosen in the following phase. In fact, the physicians must attempt personalizing the treatment based on the measurement of HbA1c, the body weight gain and the vascular damage. Despite all this, diabetes is a disease which progresses and a loss of beta cell mass occurs which leads to the need to treat with insulin. Between the arrival of the treatment with insulin and the loss of activity of oral drugs, there was no therapeutic option which could solve both the deterioration of the insulin-secreting cells and the improvement in insulin secretion, focusing it only on the hyperglycemic episodes to prevent the hypoglycemias which limit the life of diabetic patients. This therapeutic niche was covered with the discovery of the glucagon-like peptide and the development of therapeutic strategies aimed at favoring its physiological action (Best Practice & Research Clinical Endocrinology & Metabolism 23 (2009) 413-424).

The glucagon-like peptide type 1 (GLP-1) is a gastrointestinal peptide which is released by cells of the intestine and the endocrine pancreas in response to the elevation of certain nutrients in the plasma (for example, glucose). This peptide acts both in the free terminals of the peripheral sensory system innerving the intestine and in the insulin-secreting cells of the pancreatic islets of Langerhans. Their actions are triple, on one hand, inhibiting intestinal motility, by reducing the absorption of glucose, reducing intake by means of a net reduction of the appetite and, on the other hand, enhancing glucose-dependent insulin release. In other words, it acts only when the glucose is elevated, therefore its efficacy as an insulin-releasing agent is not accompanied by the induction of hypoglycemias. This action selectivity defines a special subtype of physiological signals which are generically referred to as incretins (Cell Metab 2006; 3: 153-65) and are defined as those signals capable of increasing insulin release only in hyperglycemic conditions (See monograph Best Practice & Research Clinical Endocrinology & Metabolism 23 (2009).

The incretin function of GLP-1 is preserved in Diabetes. This fact has allowed designing therapeutic strategies based on drugs which directly or indirectly activate the GLP-1 receptor in the pancreatic cell (Lancet 2006; 368: 1696-1705). Due to the physiological actions of GLP-1, a drug based on its function could exert the following actions:
  a. Releasing insulin when the blood glucose is high without doing so when its levels are low. This would reduce the risks of hypoglycemias of current treatments.
  b. Preserving the beta cell mass of the endocrine pancreas due to its trophic action thereon.
  c. Decreasing the intestinal motility, preventing sudden rises of the glycemia.
  d. Reducing or maintaining the body weight due to its satiating actions.

These actions have achieved the authorization of two types of medicinal products based on the actions of GLP-1 for the treatment of Diabetes:
  a. GLP-1 degradation inhibitors (Reviewed in Best Practice & Research Clinical Endocrinology & Metabolism 23 (2009) 479-486). The half-life of this peptide in blood is very low, 1 minute, due to the action of dipeptidyl peptidase type IV (DPPIV) present in blood and target tissues of GLP-1. There are three developed selective inhibitor drugs of this enzyme: Vidalgliptin (Galvus, Novartis, patent WO2007120936-A3); Sitagliptin (Januvia, Merck, patent WO2009085990-A2), and Saxagliptin (Bristol-Myeres-Squibb, patent WO2008131149-A3). These drugs are active by oral route.

b. GLP-1 analog peptides which are resistant to the degradation by DPPIV. (Reviewed in Lancet 2009; 374: 39-47; Best Practice & Research Clinical Endocrinology & Metabolism 23 (2009) 463-477) Two drugs have been developed, Exenatide (Byetta, Eli Lilly, patents WO 2003011892, WO 2005023291, WO 2007024700) and Liraglutide (Victoza, Novo-Nordisk, WO 2001035988). Both types of compounds must be injected in a parenteral formulation.

These drugs cover the need to treat diabetic patients in whom the drugs used in the traditional algorithms fail (for example, metformin+associated antidiabetic drug) and in whom the intention is to achieve a HBA1c<6.5%, preserving the beta cell mass and with the capacity to prevent hypoglycemias and the obesity associated with said treatments as a complication.

A third class of drugs would correspond to the allosteric modulators of the GLP-1 receptor. This class of molecules would correspond to chemical structures or biological drugs (for example antibodies) with the capacity to interact with the GLP-1 receptor in a site of the receptor different from that used by the endogenous GLP-1 peptide or the exogenous agonists thereof, and with an activity enhancing the actions of these agonists. Only one embodiment, included in the patent of a monoclonal antibody with modulator capacity for the GLP-1 receptor (US 20060275288), has been protected to date.

There are no non-peptide compounds with activity as agonists, allosteric modulators or antagonists of the GLP-1 receptor which have been approved for their use in humans. Non-peptide molecules with agonist capacity for the GLP-1 receptor (WO2005056537-A1, WO20066003096-A1) or antagonist capacity for a physiologically related hormone, glucagon (Patent WO2007123581-A1), have been described.

BRIEF DESCRIPTION OF THE INVENTION

The invention relates to the usefulness of molecules derived from 1,2,4 oxadiazole as modulators of the biological responses mediated by the GLP-1 peptide receptor, with allosteric modulator, agonist or antagonist capacity for the responses mediated by this peptide.

As a consequence, these compounds can be used for the preparation of a medicinal product for inducing satiety and controlling intake, modulating body fat and regulating lipid metabolism as well as for the preparation of a medicinal product for the prevention and/or the treatment of eating disorders or diseases, such as diabetes, obesity, anorexia, lipid dysfunction, hyperinsulinism, metabolic syndrome and cardiovascular diseases. The fundamental role of GLP-1 receptors and the agonist peptides thereof in the diseases described above is known.

According to a first aspect, the present invention relates to the use of a compound of formula (I):

wherein $R^1$ is selected from $C_6$-$C_{15}$ aryl, $C_3$-$C_{15}$ heteroaryl, $C_7$-$C_{15}$ arylalkyl and $C_3$-$C_{15}$ heteroarylalkyl;

$R^2$ is selected from hydrogen, $C_1$-$C_6$ alkyl and $C_2$-$C_6$ alkenyl;

each $R^3$ is independently selected from the group consisting of $C_1$-$C_6$ alkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, $C_3$-$C_{15}$ heterocyclylalkyl, —$OR^5$, —$SR^5$, —$S(O)R^5$, —$S(O)_2R^5$, —$OS(O)_2R^5$, —$(CH_2)_n$—$N(R^5)(R^6)$, —$C(O)R^5$, —$C(O)OR^5$, —$(CH_2)_n$—$C(O)N(R^5)(R^6)$, —$OC(O)R^5$ and —$(CH_2)_n$—$N(R^5)C(O)R^6$, $R^5$ and $R^6$ are independently selected from the group consisting of hydrogen, $C_1$-$C_6$ alkyl, $C_3$-$C_7$ cycloalkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, —$S(O)_2R^9$, —$N(H)(R^9)$;

$R^9$ is independently selected from the group consisting of $C_1$-$C_3$ alkyl, $C_6$-$C_{10}$ aryl, $C_7$-$C_{11}$ arylalkyl and an amino acid; each of these groups being able to be optionally substituted with a group which is selected from $C_1$-$C_6$ alkyl, $C_1$-$C_6$ haloalkyl, $C_2$-$C_6$ alkenyl, $C_2$-$C_6$ alkynyl, —$OR^7$, —$SR^7$, —$S(O)R^7$, —$S(O)_2R^7$, —$OS(O)_2R^7$, —$N(R^7)(R^8)$, —$C(O)R^7$, —$C(O)OR^8$, —$C(O)N(R^7)(R^8)$, —$OC(O)R^7$ and —$N(R^7)C(O)R^8$; $R^7$ and $R^8$ being independently selected from the group consisting of $C_1$-$C_3$ alkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, $C_3$-$C_{15}$ heterocyclylalkyl; optionally substituted with $C_1$-$C_3$ alkyl, $C_1$-$C_3$ haloalkyl or —O—($C_1$-$C_3$) alkyl;

y is 1, 2, 3, 4 or 5; and n is 0, 1 or 2;

or a pharmaceutically acceptable salt or solvate thereof, in the preparation of a medicinal product for the prevention and/or the treatment of a disease in which GLP-1 receptor participates or mediates.

This aspect includes a compound of formula (I), as it has been defined above, a pharmaceutically acceptable salt or solvate thereof, for its use in the prevention and/or the treatment of a disease in which the GLP-1 receptor participates or mediates.

In a particular embodiment, the disease in which the GLP-1 receptor participates or mediates is an eating disorder or disease, preferably obesity, anorexia, lipid dysfunction, diabetes, hyperinsulinism, cardiovascular diseases and metabolic syndrome. In a more preferred embodiment, the eating disorder or disease is diabetes.

Another particular embodiment relates to the use of a compound of formula (I) for reducing body fat. In a particular embodiment, said fat is selected from subcutaneous fat and visceral fat. Another particular embodiment relates to the use of a compound of formula (I) for inducing satiety and controlling intake.

An additional aspect of the invention is a compound of formula (I), as it has been defined above, for its use as a medicinal product.

An additional aspect of the invention is a pharmaceutical composition comprising a compound of formula (I), as it has been defined above, and a pharmaceutically acceptable vehicle.

An additional aspect of the invention is the cosmetic use of a compound of formula (I), as it has been defined above, for the treatment of a condition in which the GLP-1 receptor participates or mediates, wherein said condition is obesity.

An additional aspect of the invention is a cosmetic composition comprising a compound of formula (I), as it has been defined above, and a cosmetically acceptable vehicle.

DETAILED DESCRIPTION OF THE INVENTION

In the context of the present invention, the following terms have the meaning which is detailed below.

The term "alkyl" refers, in the present invention, to linear or branched hydrocarbon chain radicals which are attached to rest of the molecule by means of a single bond, for example, methyl, ethyl, n-propyl, i-propyl, n-butyl, tert-butyl, sec-butyl, n-pentyl, n-hexyl, etc.

The terms "alkenyl" and "alkynyl" refer to a linear or branched hydrocarbon chain radical which contains one or more double or triple carbon-carbon bonds, respectively and which is attached to the rest of the molecule by means of a single bond, for example, vinyl, 1-propenyl, allyl, isoprenyl, 2-butenyl, 1,3-butadienyl, —CCH, $CH_2CCH$, $CCCH_3$, $CH_2CCCH_3$, etc.

The term "aryl" refers to an aromatic group comprising 1, 2 or 3 aromatic nuclei, optionally fused, including for example phenyl, naphthyl, diphenyl, indenyl, phenanthryl, etc.

"Heteroaryl" refers to a stable 3 to 15-membered aromatic ring radical consisting of one to five heteroatoms selected from the group consisting of nitrogen, oxygen and sulfur. In an embodiment of the invention, the heteroaryl group is a 3 to 10 or 5 to 6-membered aromatic ring radical. The heteroaryl can be a monocyclic, bicyclic or tricyclic ring system which can include fused ring systems; and the nitrogen, carbon or sulfur atoms in the heteroaryl radical can optionally be oxidized; or the nitrogen atom can optionally be quaternized. Possible examples of heteroaryl include benzimidazole, benzothiazole, furan, pyrrole, thiophene, pyridine, pyrimidine, isothiazole, isoxazole, imidazole, indole, purine, quinoline, thiadiazole.

The term "cycloalkyl" refers to a saturated or partially saturated mono- or polycyclic aliphatic group which is attached to the rest of the molecule by means of a single bond, including, for example and in a non-limiting sense, cyclopropyl, cyclohexyl, cyclopentyl, etc.

"Heterocyclyl" refers to a stable 3 to 15-membered ring radical, preferably a 3 to 10-membered ring, more preferably a 5 or 6-membered ring radical, which consists of carbon atoms and from one to five heteroatoms selected from the group consisting of nitrogen, oxygen and sulfur and which can be partially or completely saturated. For the purposes of this invention, the heterocycle can be a monocyclic, bicyclic or tricyclic ring system which can include fused ring systems; and the nitrogen, carbon or sulfur atoms in the heterocyclyl radical can optionally be oxidized; and the nitrogen atom can optionally be quaternized. Examples of such heterocycles include, but are not limited to, pyrrolidine, piperidine, piperazine, morpholine, thiomorpholine, tetrahydrofuran, tetrahydroisoquinoline.

The term "arylalkyl" refers to an alkyl group substituted with an aryl group as it was defined above.

Examples of such groups include, but are not limited to, benzyl, phenylethyl, phenylpropyl, naphthylmethyl, etc.

The term "heteroarylalkyl" refers to an alkyl group substituted with a heteroaryl group as it was defined above.

The term "heterocyclylalkyl" refers to an alkyl group substituted with a heterocyclyl group as it was defined above.

The term "haloalkyl" refers to an alkyl group as it was defined above, wherein at least one of the hydrogen atoms has been substituted with a halogen group, for example $CF_3$, $CCl_3$, $CHF_2$, $CF_2CF_3$, etc.

In a particular embodiment, $R^1$ is selected from $C_6$-$C_{15}$ aryl, $C_3$-$C_{15}$ heteroaryl, $C_7$-$C_{15}$ arylalkyl and $C_3$-$C_{15}$ heteroarylalkyl; optionally substituted with $C_1$-$C_3$ alkyl, $C_1$-$C_3$ haloalkyl, —$OR^7$ or —$SR^7$, wherein $R^7$ is as defined in claim 1.

In another particular embodiment, $R^1$ is a compound of general formula (II):

wherein
n is 0, 1, 2, 3 or 4, preferably 0 or 1,
m is 0, 1, 2, 3, 4 or 5, preferably 0, 1 or 2, and
$R^4$ is selected from the group consisting of $C_1$-$C_3$ alkyl, $C_1$-$C_3$ haloalkyl, —$OR^7$, —$SR^7$; $R^7$ being selected from the group consisting of $C_1$-$C_3$ alkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroaryla- lkyl, $C_3$-$C_{15}$ heterocyclylalkyl. Preferably, $R^4$ is selected from trifluoromethyl, methoxyl, halogen, acetyl, methoxycarbonyl and methyl.

More preferably, $R^1$ is selected from

According to another particular embodiment, each $R^3$ is independently selected from the group consisting of:
$C_2$-$C_{15}$ heterocyclyl,
$C_3$-$C_{15}$ heteroaryl,
$C_3$-$C_{15}$ heterocyclylalkyl,
$C_1$-$C_6$ alkyl, optionally substituted with —N($R^7$)($R^8$), —C(O)$R^7$, —N($R^7$)C(O)$R^8$, a 5 or 6-membered heterocycle, 5 or 6-membered heteroaryl, —O$R^7$;
—O$R^5$,
—C(O)$R^5$,
—C(O)N($R^5$) ($R^6$), and
—N($R^5$) ($R^6$)
wherein $R^5$, $R^6$, $R^7$ and $R^8$ are as defined above.

Preferably, each $R^3$ is independently selected from:

According to a particular embodiment of the invention, $R^2$ is hydrogen.

According to another particular embodiment of the invention, $R^3$ is selected from the group consisting of —N(H)C(O)N(H)$R^9$, —CH$_2$N(H)C(O)N(H)$R^9$, —CH$_2$N(H)C(O)$R^9$, —CH$_2$N(H)S(O)$_2$$R^9$, —C(O)N(H)S(O)$_2$$R^9$ and —CH$_2$C(O)N(H)S(O)$_2$$R^9$.

In a preferred embodiment of the invention, y is 1 or 2, more preferably 1. According to another particular embodiment, $R^3$ is in the para position with respect to the nitrogen of the morpholine group. According to another particular embodiment, $R^3$ is in the meta position with respect to the nitrogen of the morpholine group.

In another particular embodiment, the compound of formula (I) is selected from the group consisting of:

or a stereoisomer, a pharmaceutically acceptable solvate or salt thereof.

In another preferred embodiment, the compound of general formula (I) refers to a compound which is selected from the following group:

C1
3-phenyl-1-[(3R)-1-[[3-[4-(trifluoromethyl)phenyl]-1,2,4-oxadiazol-5-yl]methyl]piperidin-3-yl]propan-1-one,
C3
N-[2-[(2S)-1-[[3-[4-(trifluoromethyl)phenyl]-1,2,4-oxadiazol-5-yl]methyl]piperidin-2-yl]ethyl]acetamide,
C4
1[[3-[4-(trifluoromethyl)phenyl]-1,2,4-oxadiazol-5-yl]methyl]piperidin-4-carboxamide,
C5
5-[[(2S)-2-(2-pyridin-2-ylethyl)piperidin-1-yl]methyl]-3-[4-(trifluoromethyl)phenyl]-1,2,4-oxadiazole,
C6
4-[[1[[3-[4-(trifluoromethyl)phenyl]-1,2,4-oxadiazol-5-yl]methyl]piperidin-3-yl]methyl]morpholine,
C7
5-[[(3S)-3-[(4-methoxyphenoxy)methyl]piperidin-1-yl]methyl]-3-[4-(trifluoromethyl)phenyl]-1,2,4-oxadiazole,
C8
5-[(4-thiomorpholin-4-ylpiperidin-1-yl)methyl]-3-[4-(trifluoromethyl)phenyl]-1,2,4-oxadiazole,
C9
phenyl-[(3R)-1-[[3[[3-[4-(trifluoromethyl)phenyl]-1,2,4-oxadiazol-5-yl]methyl]piperidin-3-yl]methanone,
C10
5-[[4-(pyridin-2-ylmethoxy)piperidin-1-yl]methyl]-3-[4-(trifluoromethyl)phenyl]-1,2,4-oxadiazole,
C11
3-benzyl-5-[[4-(3,4-dihydro-1H-isoquinolin-2-yl)piperidin-1-yl]methyl]-1,2,4-oxadiazole, and
C12
(3R)-1-[[[[3-[4-(trifluoromethyl)phenyl]-1,2,4-oxadiazol-5-yl]methyl]piperidin-3-carboxamide.

or a pharmaceutically acceptable solvate or salt thereof.

The compounds of the present invention represented by formula (I) can include isomers, depending on the presence of multiple bonds, including optical isomers or enantiomers, depending on the presence of chiral centers. The individual isomers, enantiomers or diastereoisomers and the mixtures thereof fall within the scope of the present invention, i.e., the term isomer also refers to any mixture of isomers, such as diastereomers, racemates, etc., even to their optically active isomers or the mixtures in different proportions thereof. The individual enantiomers or diastereoisomers, as well as their mixtures, can be separated by means of conventional techniques.

The compounds of the invention can be in crystalline form as free compounds or as solvates. In this sense, the term "solvate", as used herein, refers to any form of the active compound having another solvent molecule attached thereto by means of a non-covalent bond, includes both pharmaceutically acceptable solvates, i.e., solvates of the compound of formula (I) which can be used in the preparation of a medicinal product, and non-pharmaceutically acceptable solvates, which can be used in the preparation of pharmaceutically acceptable solvates or salts. The nature of the pharmaceutically acceptable solvate is not critical provided that it is pharmaceutically acceptable. In a particular embodiment, the solvate is a hydrate or an alcoholate. The solvates can be obtained by conventional solvation methods known by the persons skilled in the art.

For their application in therapy, the compounds of formula (I), the salts or solvates thereof, will preferably be in a pharmaceutically acceptable or substantially pure form, i.e., having a pharmaceutically acceptable purity level excluding the normal pharmaceutical additives such as diluents and carriers, and not including material considered to be toxic at normal dosage levels. The purity levels for the active ingredient are preferably greater than 50%, more preferably greater than 70%, and still more preferably greater than 90%. In a preferred embodiment, they are greater than 95% of compound of formula (I), or of the salts, solvates or prodrugs thereof.

For example, pharmaceutically acceptable salts of compounds provided herein are synthesized from the original compound which contains an acid or basic moiety by means of conventional chemical methods. Generally such salts are prepared, for example, by reacting the free acid or base forms of these compounds with a stoichiometric amount of the suitable base or acid in water or in an organic solvent or in a mixture of the two. Non-aqueous media such as ether, ethyl acetate, ethanol, isopropanol or acetonitrile are generally preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate and p-toluenesulfonate. Examples of alkali additional salts include inorganic salts such as, for example, sodium, potassium, calcium, ammonium, magnesium, aluminium and lithium salts, and organic alkaline salts such as, for example, ethylenediamine, ethanolamine, N,N-dialkyleneethanolamine, triethanolamine, glucamine and basic amino acid salts. Preferably, as used herein, the term "pharmaceutically acceptable" means approved by a regulatory agency of the federal government or of a state or listed in the U.S. Pharmacopoeia or another generally recognized pharmacopoeia for its use in animals and more particularly in humans.

Unless otherwise established, the compounds of the invention also include compounds which differ only in the presence of one or more isotopically enriched atoms. For example, compounds having the present structures except for the substitution of a hydrogen with a deuterium or tritium, or the substitution of a carbon enriched with $^{13}C$ or $^{14}C$ or nitrogen enriched with $^{15}N$ are within the scope of this invention.

The compounds of the present invention were commercially obtained (Chembridge, California). Alternatively, the compounds of the invention can be prepared according to the following synthetic scheme, using commercial reagents and following commonly accepted methods known by the person skilled in the art:

The initial material (1) is commercially available (for example 4-(dimethylamino)piperidine, from ChemBridge Corporation, 16981 Via Tazon, Suite G, San Diego, Calif. 92127). The piperidine can be transformed into the ester (2), for example by means of reaction with ethyl bromoacetate, and subsequently into the corresponding acid derivative, such as for example into the acid chloride, by means of hydrolysis of the ester to acid and subsequent reaction with a halogenating agent such as $SOCl_2$, $PCl_5$, $COCl_2$ or $PBr_3$.

Likewise, material (3) can be found commercially (for example 4-(trifluoromethyl)benzonitrile or benzyl cyanide, from Sigma Aldrich, 3050 Spruce St, St. Louis, 6310 USA). The 1,2,4 oxadiazole derivative can be obtained as described by Almstead, N et al. in WO2008030570-A1, by means of the reaction of the cyano group with hydroxylamine, the acylation with the acid halide derived from the compounds (2), followed by cyclization.

In another aspect, the present invention also relates to the use of pharmaceutical compositions comprising at least one compound of the invention as described above, or a pharmaceutically acceptable salt or solvate thereof, together with a carrier, an excipient or a pharmaceutically acceptable vehicle, in the preparation of a medicinal product for the prevention and/or the treatment of a disease in which the GLP-1 receptor participates or mediates. Preferably, for the prevention and/or the treatment of an eating disorder or disease, preferably obesity, anorexia, lipid dysfunction, diabetes, hyperinsulinism, cardiovascular diseases and metabolic syndrome. In a more preferred embodiment, the eating disorder or disease is diabetes, or for reducing subcutaneous fat and/or for inducing satiety and controlling intake.

The pharmaceutical compositions according to the present invention can be found in any suitable form for their administration to humans and/or animals, preferably humans, including babies, children and adults and can be prepared by standard processes known by the persons skilled in the art. They can be prepared by standard processes known by the persons skilled in the art, for example, from the index of "Pharmaceutics: The Science of Dosage Forms, second edition, Aulton, M. E. (ed.) Churchill Livingstone, Edinburgh (2002); "Encyclopedia of Pharmaceutical Technology", second edition, Swarbrick, J. and Boylan J. C. (eds.), Marcel Dekker, Inc. Nueva York (2002); "Modern Pharmaceutics", fourth edition, Banker G. S, and Rhodes C. T. (eds.) Marcel Dekker, Inc. New York 2002 and "The Theory and Practice of Industrial Pharmacy", Lachman L., Lieberman H. and Kanig J. (eds.), Lea & Febiger, Philadelphia (1986). The respective descriptions are incorporated in this document by reference and form part of the description. The composition of the pharmaceutical composition can vary depending on the route of administration.

The pharmaceutical composition of the invention can be administered in a plurality of pharmaceutical dosage forms, for example, solids and liquids, etc. Illustrative non-limiting examples of said pharmaceutical dosage forms of the pharmaceutical composition of the invention include:

oral formulations (liquids, solution, suspension, emulsion, gel, paste, powder, etc.); solid formulations, such as tablets (for example, soluble tablet, dispersible tablet, coated tablet, film-coated tablet, effervescent tablet, orodispersible tablet, gastro-resistant tablet, prolonged-release tablet, modified-release tablet, buccal tablet, chewable tablet, etc.); capsules (for example, hard, soft, gastro-resistant hard or soft capsule, prolonged-release hard or soft capsule, modified-release hard or soft capsule, etc.); pills;

transdermal patches;

creams;

suppositories; or for intraperitoneal administration.

The term "vehicle" refers to a diluent, adjuvant, excipient or vehicle with which the active ingredient is administered. Such pharmaceutical vehicles can be sterile liquids, such as water or oils, including those of petroliferous, animal, vegetal or synthetic origin, such as peanut oil, soybean oil, mineral oil, sesame oil and the like. Water or aqueous solution salines and aqueous solutions of dextrose and glycerol, particularly for injectable solutions, are preferably used as vehicles. Suitable pharmaceutical vehicles are described in "Remington's Pharmaceutical Sciences" by E. W. Martin.

The compounds described in the present invention, the salts and/or solvates thereof as well as the pharmaceutical compositions containing them can be used together with other additional drugs or active ingredients to provide a combination therapy. Said additional drugs can form part of the same pharmaceutical composition or, alternatively, they can be provided in the form of a separate composition for its simultaneous or non-simultaneous administration with respect to that of the pharmaceutical composition comprising a compound of formula (I), or a salt, prodrug or solvate thereof. In a preferred embodiment, the pharmaceutical composition comprises another active ingredient selected from the following list:

a. Protease-resistant GLP-1 receptor agonists
b. Inhibitors of proteases NEP and DPPIV
c. GLP-1 secretagogs
d. Sulfonylureas
e. Biguanides including metformin
f. Metiglinides
g. Thiazolidinediones
h. Alpha-glucosidase inhibitors
i. Human insulin and human insulin analogs
j. Hypolipidemic drugs including statins, and alpha, gamma and delta subtype peroxisome proliferator receptor agonists.

In the sense used in this description, the expression "therapeutically effective amount" refers to the amount of the agent or compound capable of developing the therapeutic action determined by its pharmacological properties, calculated to produce the desired effect and it will generally be determined, among other causes, by the own characteristics of the compounds, including the age, condition of the patient, the severity of the alteration or disorder, and the route and frequency of administration.

The administered amount of a compound of the present invention will depend on the relative efficacy of the chosen compound, the severity of the disease to be treated and the weight of the patient. However, the compounds of this invention will be administered one or more times a day, for example 1, 2, 3 or 4 times daily, with a total dose between 0.1 and 1000 mg/Kg/day. It is important to take into account that it may be necessary to introduce variations in the dose, depending on the age and on the condition of the patient, as well as modifications in the route of administration.

Throughout the description and the claims, the word "comprises" and its variants do not intend to exclude other technical features, additives, components or steps. For the persons skilled in the art, other objects, advantages and features of the invention will be inferred partly from the description and partly from the practice of the invention. The following examples and figures are provided by way of illustration and are not intended to limit the present invention.

EXAMPLES

A series of examples is shown below, which examples are set forth at all times to illustrate the general experimental procedures supporting the claims. According to the above, the following section of examples by no means intends to limit the scope of the invention contemplated in the present specification.

In this specification, the symbols and conventions used in these procedures, schemes and examples are consistent with those used in the International System and contemporary scientific literature, for example, the Journal of Medicinal Chemistry. Unless otherwise indicated, all the starting materials were obtained from commercial suppliers (Sigma Chemicals (Chemical reagents and culture media, general laboratory products; Invitrogen (Culture media), Tocris Cookson (GLP-1 and Exendin 4); Harlan (animals)) and were used without additional purification. Specifically, the following abbreviations can be used in the examples and throughout the entire specification: g (grams); mg (milligrams); kg (kilograms); µg (micrograms); L (liters); mL (milliliters); µL (microliters); mmol (millimoles); mol (moles); ° C. (degrees Celsius); M (molar); DMSO (dimethylsulfoxide); PBS (phosphate-buffered saline). The specific compounds that the experiments and figures refer to are compounds C1 to C12 mentioned above.

In Vivo Experiments

All the in vivo experiments were performed using male Wistar rats with a weight of 200-450 g. The animals were housed in individual cages in a room with controlled temperature (23° C.) and humidity (50%) with a 12/12 light and dark cycle. The animals had water and food ad libitum except in specific experimental procedures. The animals were handled once a day during the two days before the experimental sessions. All the products were dissolved in a mixture of 5% DMSO, 5% Tween 60/90% saline and intraperitoneally administered. The vehicle was 0.9% sterile saline for the parenteral glucose overload.

Intake Control Assay

Figure 1:
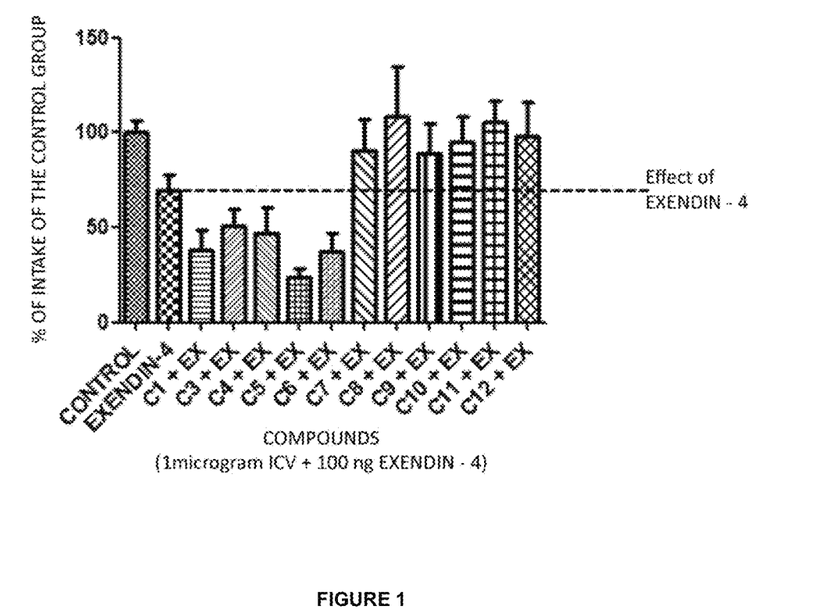
FIG. 1—Compounds which enhance satiety mediated by a GLP-1 receptor agonist (Exendin 4) and compounds which antagonize satiety mediated by a GLP-1 receptor agonist (Exendin 4). Compounds C1 to C6 detailed in this invention enhance the decrease of food intake induced by Exendin 4, whereas compounds C7 to C12 antagonize it.

The acute effect on the intake of all the products was tested in animals which had fasted for 24 hours. Thirty minutes after the injection, the previously weighed food was replaced in the cage. The food was weighed 30, 60, 120 and 240 minutes after the start of the test. All the intake experiments were performed with groups of 8 animals (n=8) (FIG. 1). In the experiments for the identification of candidate compounds, those compounds capable of enhancing the effects of reducing the intake of a dose of the GLP-1 or Exendin 4 agonist which causes 50% of the maximum effect were sought. This strategy allows identifying the compounds which enhance or inhibit the actions of the GLP-1 receptor agonists (see FIG. 1) and checking if they are active per se or are allosteric modulators of the actions of the mentioned peptides.

In Vitro Insulin Secretion Assay

Figure 2:
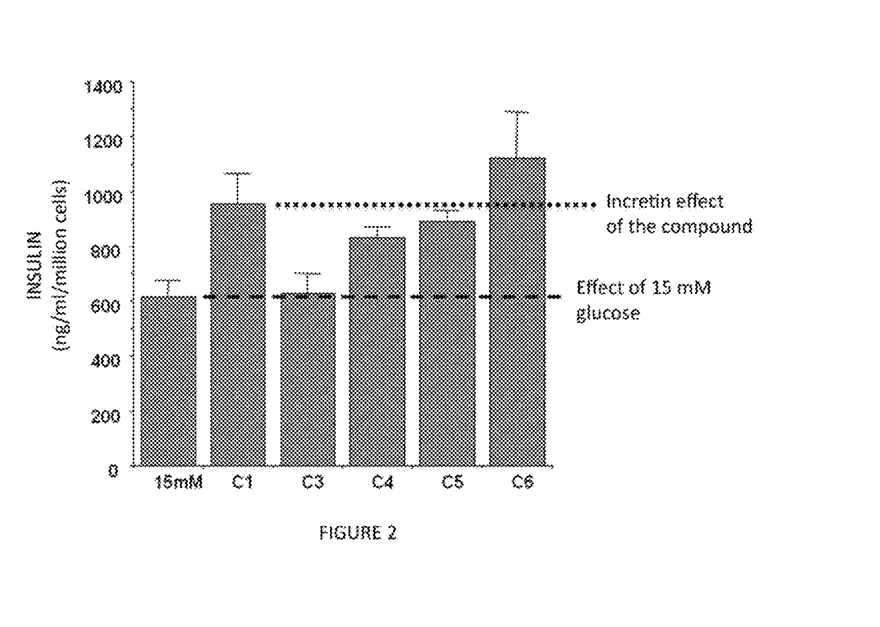
FIG. 2—In vitro activation in rat insulinoma cells of the insulin secretion activated by selected compounds of the invention. Compounds C1, C4, C5 and C6 are direct activators of the glucose-activated insulin secretion.
Figure 3:
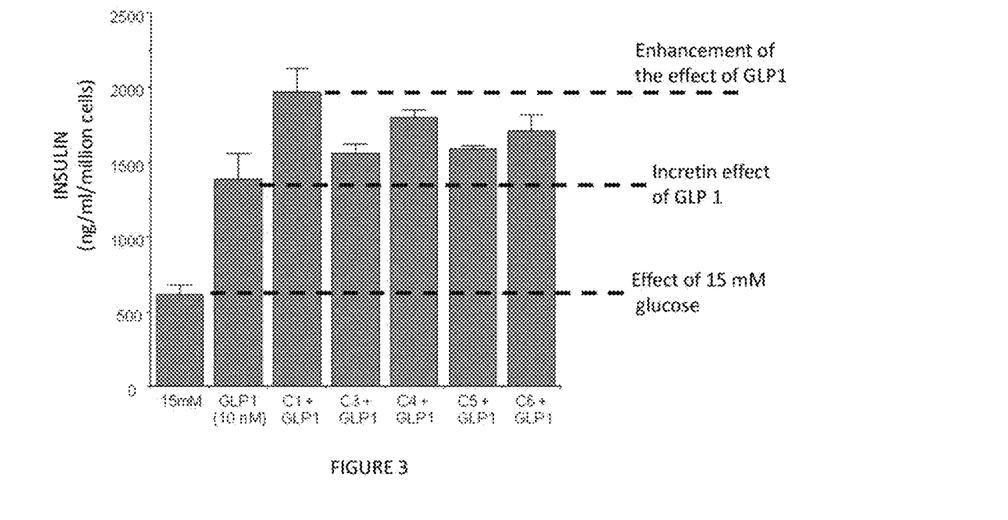
FIG. 3—Compounds which enhance GLP-1-activated insulin secretion. Compounds C1, C3, C4, C5 and C6 of the invention enhance the glucose-dependent insulin release caused by GLP-1 (10 nM) in rat insulinoma cells.
Figure 4:
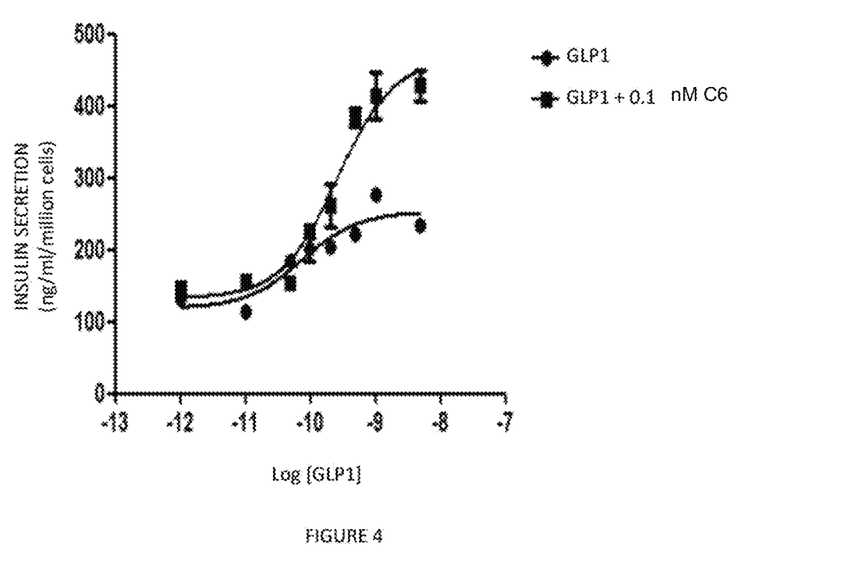
FIG. 4—Allosteric modulation of GLP-1-stimulated insulin secretion. Compound C6 at a concentration 0.1 nM enhances the insulin release stimulated by increasing doses of GLP-1 in insulinoma cells.
Figure 5:
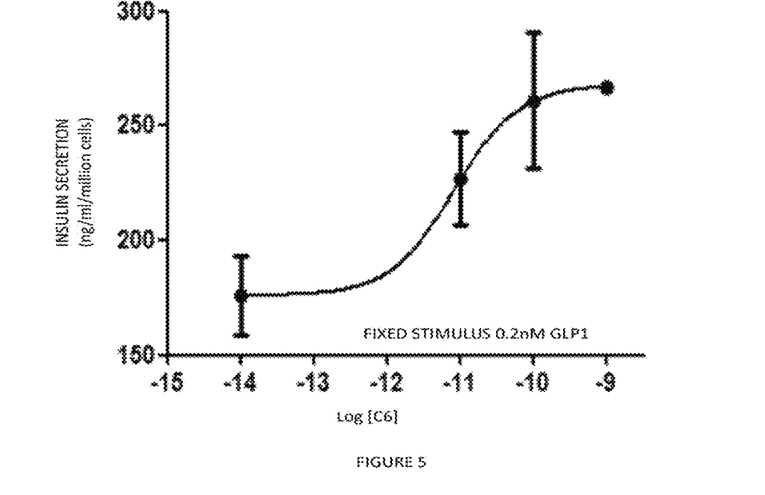
FIG. 5—Allosteric modulation of GLP-1-stimulated insulin secretion. Compound C6 enhances in a dose-dependent manner the insulin secretion stimulated by a fixed concentration of 0.2 nM GLP-1 in insulinoma cells.

The insulin secretion studies were performed in INS1E cells cultured in RPMI 1640 medium (Invitrogen, Switzerland) containing 11 mM glucose. The culture medium was supplemented with 10 mM Hepes (pH 7.3), 10% (v/v) heat-inactivated fetal bovine serum (Brunschwig AG, Switzerland), 50 mM b-mercaptoethanol, 1 mM sodium pyruvate, 50 mg/ml penicillin and 100 mg/ml streptomycin (INS medium). Static secretion studies were performed in culture plates with a diameter of 2.5 cm in which the cells were grown until reaching confluence criteria. The in vitro studies allowed identifying compounds with intrinsic capacity to release insulin (FIG. 2) or which enhance the incretin actions of GLP-1 (FIGS. 3, 4 and 5).

Parenteral Glucose Overload Assay

Figure 6:
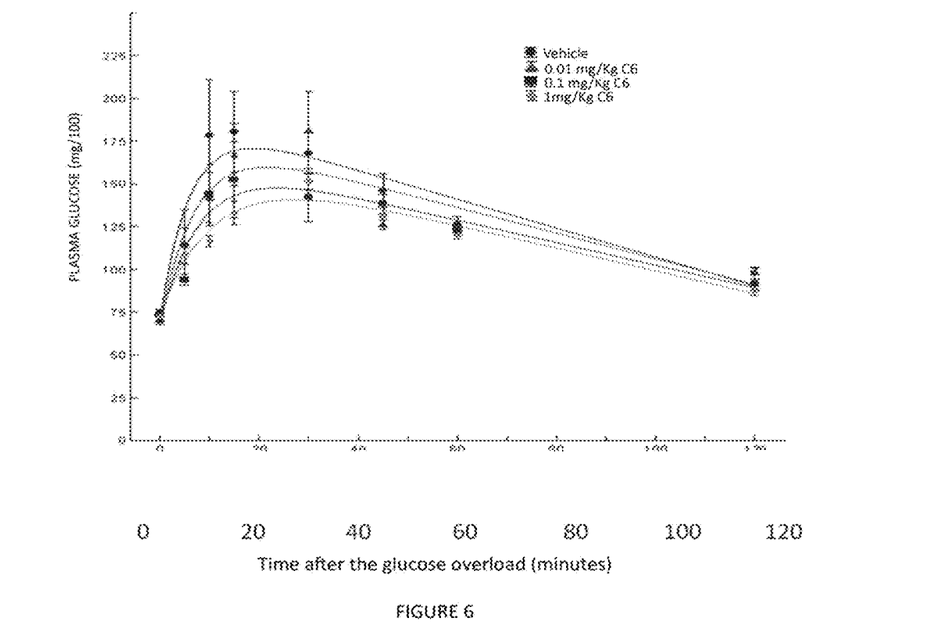
FIG. 6—Compound C6 improves the physiological response in the parenteral glucose overload test in rats. These results indicate that the direct insulin release effect caused by compound C6 in vitro also occurs in vivo.
Figure 7:
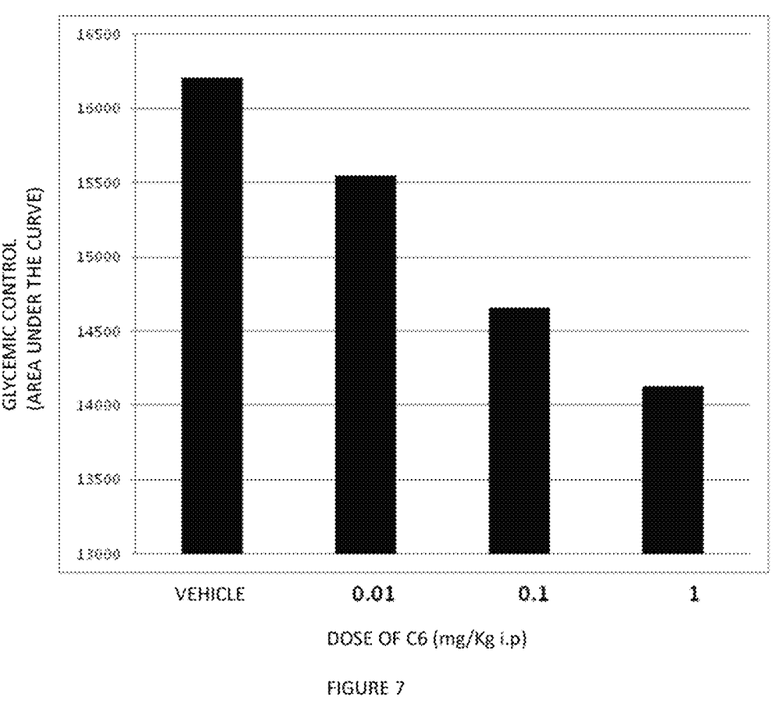
FIG. 7—Compound C6 improves the management of glycemia in the parenteral glucose overload test in rats. The compound induces in a dose-dependent manner a reduction of the intensity of the hyperglycemia, as shown by the analysis of the area under the curve of the glycemia shown in FIG. 6.

The parenteral glucose overload assay was performed in male Wistar rats (Harlan, Barcelona) deprived of food for 18 hours. The animals received an injection of sterile saline containing glucose which was administered at the dose of 2 gr/kg in a volume of 2 ml/kg. The plasma glucose levels were measured by means of glucometers in tail blood using reactive strips of glucose oxidase, at times 0, 5, 10, 15, 30, 45, 60 and 120 minutes after the administration of glucose. The animals received an injection of the drugs under study 15 minutes before the administration of intraperitoneal glucose. After measuring the glucose, an analysis under the curve for compound and dose was performed. This analysis allows evaluating the time intensity of the hyperglycemia. An embodiment for compound C6 is shown (FIGS. 6 and 7).

The invention claimed is:

1. A method for the treatment, in a mammal suffering or being susceptible to suffer from a disease in which the GLP-1 receptor participates or mediates for a) reducing body fat inducing satiety and controlling intake or for b) the treatment of a disease selected from an eating disorder and a disease selected from the list comprising obesity, anorexia, lipid dysfunction, diabetes, hyperinsulism, metabolic syndrome and cardiovascular diseases, the method comprising administering to said mammal an effective amount of a compound of formula (I):

together with a pharmaceutically acceptable vehicle, wherein $R^1$ is selected from $C_6$-$C_{15}$ aryl, $C_3$-$C_{15}$ heteroaryl, $C_7$-$C_{15}$ arylalkyl and $C_3$-$C_{15}$ heteroarylalkyl;

$R^2$ is selected from hydrogen, $C_1$-$C_6$ alkyl and $C_2$-$C_6$ alkenyl;

wherein each $R^3$ is independently selected from the group consisting of:

$C_2$-$C_{15}$ heterocyclyl, $C_3$-$C_{15}$ heteroaryl, $C_3$-$C_{15}$ heterocyclylalkyl, $C_1$-$C_6$ alkyl, optionally substituted with —N($R^7$)($R^8$), —C(O)$R^7$, a 5 or 6-membered heterocycle, 5 or 6-membered heteroaryl, —O$R^7$;

—O$R^5$

—C(O)$R^5$,

—C(O)N($R^5$)($R^6$), and

—N($R^5$)($R^6$), $R^5$ and $R^6$ are independently selected from the group consisting of hydrogen, $C_1$-$C_6$ alkyl, $C_3$-$C_7$ cycloalkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, —S(O)$_2$$R^9$, —N(H)($R^9$);

$R^9$ is independently selected from the group consisting of $C_1$-$C_3$ alkyl, $C_6$-$C_{10}$ aryl, $C_7$-$C_{11}$ arylalkyl and an amino acid;

each of these groups being able to be optionally substituted with a group which is selected from $C_1$-$C_6$ alkyl, $C_1$-$C_6$ haloalkyl, $C_2$-$C_6$ alkenyl, $C_2$-$C_6$ alkynyl, —O$R^7$, —S$R^7$, —S(O)$R^7$, —S(O)$_2$$R^7$, —OS(O)$_2$$R^7$, —N($R^7$)($R^8$), —C(O)$R^7$, —C(O)O$R^8$, —C(O)N($R^7$)($R^8$), —OC(O)$R^7$ and —N($R^7$)C(O)$R^8$; $R^7$ and $R^8$ being independently selected from the group consisting of $C_1$-$C_3$ alkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, $C_3$-$C_{15}$ heterocyclylalkyl; optionally substituted with $C_1$-$C_3$ alkyl, $C_1$-$C_3$ haloalkyl or —O—($C_1$-$C_3$)alkyl;

y is 1, 2, 3, 4 or 5; and or a pharmaceutically acceptable solvate or salt thereof.

2. The method according to claim 1, wherein $R^1$ is selected from $C_6$-$C_{15}$ aryl, $C_3$-$C_{15}$ heteroaryl, $C_7$-$C_{15}$ arylalkyl and $C_3$-$C_{15}$ heteroarylalkyl; optionally substituted with $C_1$-$C_3$ alkyl, $C_1$-$C_3$ haloalkyl, —O$R^7$ or —S$R^7$, wherein $R^7$ is as defined in claim 1.

3. The method according to claim 2, wherein $R^1$ is a radical of general formula (II):

(II)

wherein n is 0, 1, 2, 3 or 4, m is 0, 1, 2, 3, 4 or 5, and

$R^4$ is selected from the group consisting of $C_1$-$C_3$ alkyl, $C_1$-$C_3$ haloalkyl, —O$R^7$, —S$R^7$; $R^7$ being selected from the group consisting of $C_1$-$C_3$ alkyl, $C_6$-$C_{15}$ aryl, $C_3$-$C_{15}$ heteroaryl, $C_2$-$C_{15}$ heterocyclyl, $C_7$-$C_{15}$ arylalkyl, $C_3$-$C_{15}$ heteroarylalkyl, $C_3$-$C_{15}$ heterocyclylalkyl.

4. The method according to claim 3, wherein $R^1$ is selected from

5. The method according to claim 1, wherein each $R^3$ is independently selected from:

6. The method according to claim 1, wherein $R^2$ is hydrogen.

7. The method according to claim 1, wherein y is 1 or 2.

8. The method according to claim 1, wherein the compound of formula (I) is selected from:

,

, and

-continued the stereoisomers thereof, or a pharmaceutically acceptable solvate or salt thereof.

9. The method according to claim 1, wherein the compound of formula (I) is selected from:
- -3-phenyl-1-[(3R)-1-[[3-[4-(trifluoromethyl)phenyl]-1,2,4-oxadiazol-5-yl]methyl]piperidin-3-yl]propan-1-one,
- 1[[3-[4-(trifluoromethyl)phenyl]-1,2,4-oxadiazol-5-yl]methyl]piperidin-4-carboxamide,
- 5-[[(2S)-2-(2-pyridin-2-ylethyl)piperidin-1-yl]methyl]-3-[4-(trifluoromethyl)phenyl]-1,2,4-oxadiazole,
- 4-[[1-[[3-[4-(trifluoromethyl)phenyl]-1,2,4-oxadiazol-5-yl]methyl]piperidin-3-yl]methyl]morpholine,
- 5-[[(3S)-3-[(4-methoxyphenoxy)methyl]piperidin-1-yl]methyl]-3-[4-(trifluoromethyl)phenyl]-1,2,4-oxadiazole,
- 5-[(4-thiomorpholin-4-ylpiperidin-1-yl)methyl]-3-[4-(trifluoromethyl)phenyl]-1,2,4-oxadiazole,
- phenyl-[(3R)-1-[[3-[3-[4-(trifluoromethyl)phenyl]-1,2,4-oxadiazol-5-yl]methyl]piperidin-3-yl]methanone,
- 5-[[4-(pyridin-2-ylmethoxy)piperidin-1-yl]methyl]-3-[4-(trifluoromethyl)phenyl]-1,2,4-oxadiazole,
- 3-benzyl-5-[[4-(3,4-dihydro-1H-isoquinolin-2-yl)piperidin-1-yl]methyl]-1,2,4-oxadiazole, and
- (3R)-1-[[[3-[4-(trifluoromethyl)phenyl]-1,2,4-oxadiazol-5-yl]methyl]piperidin-3-carboxamide, or a pharmaceutically acceptable solvate or salt thereof.

10. A cosmetic method for the treatment of a condition in which the GLP-1 receptor participates or mediates, wherein said condition is obesity, the method comprising administering to said mammal an effective amount of a compound of formula (I) as defined in claim 1 together with a pharmaceutically acceptable vehicle.

11. A cosmetic composition comprising a compound of formula (I) as defined in claim 1 and a cosmetically acceptable vehicle.

* * * * *